United States Patent
Gonzalez et al.

(10) Patent No.: US 10,793,908 B2
(45) Date of Patent: Oct. 6, 2020

(54) METHOD FOR THE DIAGNOSIS OF DISORDERS CAUSED BY FETAL ALCOHOL SYNDROME

(71) Applicants: Centre Hospitalier Universitaire De Rouen, Rouen (FR); Universite de Rouen Normandie, Mont Saint Aignan (FR); Institut National De La Sante Et De La Recherche Medicale (INSERM), Paris (FR)

(72) Inventors: Bruno José Gonzalez, La Vaupaliere (FR); Stéphane Marret, Rouen (FR); Matthieu Jean Alexandre Lecuyer, Rouen (FR); Annie Laquerriere, Bonsecours (FR); Soumeya Bekri, St Leger du Bourg Denis (FR); Céline Lesueur, Mont Saint Aignan (FR); Sylvie Marguerite Alberte Jegou, Rouen (FR); Pascale Yvonne Joséphine Marcorelles, Brest (FR)

(73) Assignees: Centre Hospitalier Universitaire De Rouen, Rouen (FR); Universite de Rouen Normandie, Mont Saint Aignan (FR); Institut National De La Sante Et De La Recherche Medicale (INSERM), Paris (FR)

( * ) Notice: Subject to any disclaimer, the term of this patent is extended or adjusted under 35 U.S.C. 154(b) by 0 days.

(21) Appl. No.: 15/738,922

(22) PCT Filed: Jun. 22, 2016

(86) PCT No.: PCT/EP2016/064480
§ 371 (c)(1),
(2) Date: Dec. 21, 2017

(87) PCT Pub. No.: WO2016/207253
PCT Pub. Date: Dec. 29, 2016

(65) Prior Publication Data
US 2018/0195124 A1    Jul. 12, 2018

(30) Foreign Application Priority Data

Jun. 22, 2015 (FR) .................................... 15 55727

(51) Int. Cl.
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/158* (2013.01); *G01N 2333/515* (2013.01); *G01N 2800/38* (2013.01)

(58) Field of Classification Search
None
See application file for complete search history.

(56) References Cited

U.S. PATENT DOCUMENTS

2010/0311067 A1    12/2010   Redei et al.

OTHER PUBLICATIONS

Ramadoss and Magness, Physiol Genomics, 2012; 44: 622-628 (Year: 2014).*
The website downloaded Dec. 24, 2019: https://www.genomics-online.com/resources/16/5049/housekeeping-genes/; 3 pages total (Year: 2019).*
Ayakannu et al., Molecular Human Reproduction, vol. 21, No. 9 pp. 723-735, 2015 (Year: 2015).*
Helske et al., *Expression of vascular endothelial growth factor receptors 1, 2 and 3 in placentas from normal and complicated pregnancies*, 7(2) Molecular Human Reproduction 205-210 (2001).
Jégou et al., *Prenatal Alcohol Exposure Affects Vasculature Development in the Neonatal Brain*, 72(6) Annals of Neurology 952-960 (2012).
Poodeh et al., *Alcohol-induced premature permeability in mouse placenta-yolk sac barriers in vivo*, 33 Placenta 866-873 (2012).
Rosenberg et al., *Effects of moderate drinking during pregnancy on placental gene expression*, 44 Alcohol 673-690 (2010).
Vuorela et al., *Hepatocyte Growth Factor, Epidermal Growth Factor, and Placenta Growth Factor Concentrations in Peripheral Blood of Pregnant Women With Alcohol Abuse*, 26(5) Alcoholism: Clinical and Experimental Research 682-687 (2002).

* cited by examiner

*Primary Examiner* — Christina M Borgeest
(74) *Attorney, Agent, or Firm* — Panitch Schwarze Belisario & Nadel LLP

(57) ABSTRACT

The present invention provides a method for the diagnosis of disorders caused by foetal alcohol syndrome, said method comprising the assaying of PLGF (placental growth factor).

11 Claims, 12 Drawing Sheets

METHOD FOR THE DIAGNOSIS OF DISORDERS CAUSED BY FETAL ALCOHOL SYNDROME

CROSS-REFERENCE TO RELATED APPLICATIONS

This application is a U.S. National Stage Application pursuant to 35 U.S.C. § 371 of International Patent Application PCT/EP2016/064480, filed on Jun. 22, 2016, and published as WO 2016/207253 on Dec. 29, 2016, which claims priority to France Patent Application 1555727, filed on Jun. 22, 2015, all of which are incorporated herein by reference in their entireties for all purposes.

INTRODUCTION

Alcohol is a physical and behavioural teratogen. In humans, prenatal alcohol exposure can lead to alterations in brain development. Thus, alcohol consumption during pregnancy (foetal alcohol exposure) is the leading cause of handicap and especially of mental retardation of nongenetic origin in France and worldwide.

The damage varies according to the period when the foetus was exposed, the blood alcohol levels, the genetic and environmental factors, and the consumption pattern (chronic, binge drinking).

Foetal alcohol syndrome (FAS) is the most extreme and disabling manifestation of foetal alcohol spectrum disorders (FASDs). It combines physical abnormalities such as hypotrophy (growth retardation), craniofacial dysmorphism and neurobehavioural abnormalities expressed as cognitive function disorders (attention, motor, learning or memory disorders). The diagnosis of FAS children is relatively easy. Based on morphological abnormalities, it can be established in utero or at birth.

On the other hand, many FASD children do not exhibit the morphological abnormalities of FAS children, which reduces the chance of early diagnosis. Nevertheless, these children are not free of defects. These incapacities/handicaps will be detected in the first years of life (hyperactivity, attention disorders), while invaluable months of care could have been provided from the first year of life. These defects, in the long term, will be associated with social, professional and family incapacities. These children's future, and their career prospects, thus are seriously at risk. A diagnosis at birth would allow these children to receive the early interventions essential for reducing to the maximum extent possible the incapacities associated with foetal alcohol exposure.

To date, significant efforts have been undertaken to identify biomarkers of foetal alcohol exposure, i.e., markers making it possible to answer the question: was the child exposed to alcohol during its foetal life?

However, this information, although important, is itself not able to improve the care provided to infants, for several reasons. First, there is no alcohol toxicity threshold.

In other words, documented exposure will not necessarily be associated with developmental disorders in the child. Nevertheless, an episodic exposure at a key moment of neurodevelopment would not be without consequences and the concept of window of vulnerability is now widely accepted. Moreover, consumption patterns have changed dramatically. For example, in adolescents, episodic consumption, such as heavy drinking on weekends, is on the sharp increase in both girls and boys. Finally, since the exposure biomarkers developed heretofore most often target chronic exposure, there is a genuine risk of false negatives.

There is thus a need to develop biomarkers which make it possible to monitor the effects of in utero alcohol exposure.

DESCRIPTION

The present invention offers the opportunity to develop a placental biomarker of brain damage from foetal alcohol exposure. This type of biomarker has never been developed heretofore. Indeed, the current foetal alcohol biomarkers are so-called "exposure" biomarkers which make it possible to determine if the mother consumed alcohol during pregnancy or if the child was exposed in utero. However, except for the most severe cases (foetal alcohol syndrome, FAS), an exposure biomarker does not make it possible to establish the effects of in utero alcohol exposure on the brain. To date, most FASD children escape early diagnosis. Furthermore, and for obvious economic reasons, it is not possible to provide interventions for all children whose mother consumed alcohol during pregnancy.

The present invention, unlike the biomarkers of the prior art, makes it possible to monitor the effects of foetal alcohol. Indeed, the inventors showed that the assaying of PlGF makes it possible to identify, in children exposed to alcohol in utero, those children who suffered brain damage. In particular, PlGF level indicates which children have a disorganised brain vasculature, resulting from altered brain angiogenesis. To date, however, these children escape early diagnosis. The present invention thus mitigates the lack of early diagnosis observed for FASD children, who represent in France 9 cases per 1000 births and whose clinical signs (hyperactivity, attention disorders, etc.) are detected only belatedly (for example between 4 and 5 years of age, during schooling). The present invention thus makes it possible to provide early, appropriate interventions for these children. This care will notably consist of stimulating the child's motor, sensory and cognitive functions at a time (early childhood) when brain plasticity is maximum.

In a previous study (Piia Vuorela et al., Alcoholism: Clinical and Experimental Research, 2002), PlGF level was measured in the peripheral blood of alcohol-consuming pregnant women and compared with that of abstinent pregnant women. According to this study, serum PlGF concentration increases in pregnant women who consume alcohol during the second and third trimesters of pregnancy in comparison with abstinent women.

Contrary to that which was described by Piia Vuorela et al., the inventors of the present invention showed that alcohol consumption during pregnancy causes a reduction in PlGF expression in the foetus. The reduction in PlGF level is associated with a reduction in the expression of foetal brain pro-angiogenic receptors and with a reduction in foetal brain angiogenesis. The molecular effects of the reduction in PlGF level, which mimic those of foetal alcohol, shows the physiological validity of the present invention.

According to a first aspect, the invention has as an object an in vitro method for the diagnosis of foetal alcohol spectrum disorders (FASDs) in a subject, said method comprising the following steps:

a) measuring the amount of PlGF in a biological sample, and b) establishing a foetal alcohol spectrum disorder.

The term "PlGF" or "placental growth factor" (these terms are synonymous) means a protein of the vascular endothelial growth factor (VEGF) family. More particularly, PlGF within the meaning of the invention is a 149-amino acid protein highly similar to VEGF-A which is recognised by the same receptor as the latter, VEGF-R1. PlGF is strongly expressed by the placenta, but not by the foetal brain. N-terminal glycosylated PlGF is secreted and functions in dimer form to stimulate angiogenesis. The term "PlGF" means in particular all four isoforms, PlGF1-4: PlGF-1 and PlGF-3 are isoforms that do not bind heparin whereas PlGF-2 and PlGF-4 contain additional domains for binding heparin. Even more preferentially, "PlGF" means a murine protein the sequence of which is available under accession number NP_001258634 or a human protein the sequence of which is available under accession number NP_001193941.1.

The term "foetal alcohol syndrome disorders (FASDs)" means all disorders in children resulting from alcohol exposure during gestation. This term includes, inter alia, all behavioural disorders that appear progressively with age. Children with these disorders are called "FASD children". In their most severe version, FASDs correspond to foetal alcohol syndrome (FAS). The latter is expressed as a craniofacial dysmorphism (comprising shortened eye slits; a smooth, elongated, flattened nasolabial fold; and a thin upper lip); a nonspecific growth retardation (size or weight or head circumference), which may be prenatal or postnatal or both; and neurological developmental disorders sometimes expressed by mental retardation and more often by learning difficulties. Children suffering from FAS are called "FAS children".

The inventors showed that alcohol exposure causes brain vascular defects. The term "brain vascular defects", as used herein, means any alteration of the brain vasculature, especially an alteration resulting in an altered or a defective functioning of said vasculature. Brain vascular defects within the meaning of the invention may notably be a disorganisation of the brain vasculature. More particularly, foetal alcohol induces a random orientation of the brain vessels. According to a particular embodiment, the foetal alcohol spectrum disorder is related to brain vascular defects. Even more particularly, said foetal alcohol spectrum disorder is related to a disorganisation of the brain vasculature.

According to the invention, the term "subject" means a human, and preferably an embryo, a foetus or a child. The term "embryo", as used herein, means a fertilised oocyte aged less than three months. The term "foetus", as used herein, means an individual taken before birth and of which the gestational age is between 3 and 9 months. After delivery, the subject becomes a child. According to the invention, the term "child" means an individual under 3 years of age. The category comprising children according to the invention thus includes new-borns, between 0 and 1 month of age; infants, between 1 month and 2 years of age; and children themselves, 2 years of age or older. A "new-born", as used herein, may be full-term or premature.

The expression "subject with foetal alcohol spectrum disorders" or "FASD subject", as used herein, means an embryo, a foetus or a subject, in particular human, which is exposed to alcohol in utero and which suffers from foetal alcohol spectrum disorders or which is in danger of developing, because of the mother's alcohol consumption, one of the conditions related to foetal alcohol spectrum disorders, including the effects described above. In particular, an FASD subject has a disorganised brain vasculature, said disorganisation being notably related to a random orientation of the brain vessels.

The method of the invention is particularly useful because it makes it possible to predict brain defects noninvasively. Indeed, it makes it possible to detect from a biological sample, notably a placental sample, the subjects who are at risk for FASDs, which makes it possible to provide said subjects with care.

According to the invention, the term "biological sample" means any sample that can be taken from a subject. Alternatively, the biological sample is a sample of the placenta, notably of the umbilical cord. Indeed, PlGF is expressed by placental cells throughout pregnancy. This makes it possible to assay PlGF without violating the subject's integrity, in particular when the subject is an embryo or a foetus. Generally, the biological sample must make it possible to determine the expression level of the biological marker of the invention. The sample to be tested may be used as obtained directly from the biological source or following a pretreatment to modify the nature of the sample. For example, such a pretreatment may include the preparation of plasma from blood, the dilution of viscous fluids, and so on. Pretreatment processes may also involve filtration, precipitation, dilution, distillation, mixing, concentration, inactivation of disruptive components, addition of reagents, lysis, etc. In addition, it may be beneficial to modify a solid test sample in order to form a liquid medium or to release the analyte.

PlGF protein is a secreted protein (DeFalco, Exp Mol Med. 44(1): 1-9, 2012). The preferred biological samples for determining the expression level of said biomarkers comprise in particular samples of blood, plasma or lymph. Preferably, the biological sample is a blood sample. More preferably, the biological sample is a sample of placental blood or cord blood. Indeed, said sample is usually collected during delivery. Placental vessel blood can then be obtained in order to measure the PlGF level in the blood. This enables noninvasive diagnosis of a foetal alcohol spectrum disorder, notably brain damage. Indeed, the simple assaying of PlGF in the blood makes it possible to determine if in utero alcohol exposure caused FASDs, notably because of brain vascular disorganisation.

The inventors thus showed that PlGF makes it possible to determine whether brain damage has occurred, unlike the biomarkers of the prior art which detected only the foetus's exposure to alcohol. PlGF is thus a reliable biomarker of FASDs. The term "biomarker", within the meaning of the present application, means a characteristic which is objectively measured and evaluated as an indicator of normal biological processes, pathogenetic processes, or pharmacological responses to a therapeutic intervention. "Biomarker" thus means an entire range of various substances and parameters. For example, a biomarker may be a substance the detection of which indicates a particular pathological state (e.g., the presence of activated protein C as a marker of infection), or conversely a substance the detection of which indicates a specific physiological state. The biomarker according to the invention is preferentially a gene, gene products such as the transcripts of said gene and the peptides derived from the transcripts of said gene, a lipid, a sugar or a metabolite.

According to an embodiment of the present invention, the biomarker is a gene, gene products such as transcripts or peptides, a lipid, a sugar or a metabolite the changes in the expression of which, in particular the expression level, correlate with a physiological state of the child resulting from in utero alcohol exposure. According to a particular embodiment, the biomarker is a peptide having growth factor activity.

The candidate biomarker according to the invention is preferably a genetic marker, a protein marker, a lipid marker or a metabolic marker. For each of these types of markers, a number of methods are at the disposal of the person skilled in the art to measure the expression of said biomarker and thus to identify a difference in expression between children exposed to alcohol in utero and healthy children, i.e., children who were not exposed to alcohol.

In a first embodiment, said marker is a genetic marker or a protein marker.

In this case, the method of the invention may comprise one or more intermediate steps between the sampling of the skin cells and the measurement of PlGF expression, said steps corresponding to the extraction from said placental sample of an mRNA sample (or the corresponding cDNA) or a protein sample. This can then be used directly to measure PlGF expression. The preparation and extraction of mRNA (and the reverse transcription thereof into cDNA) or of proteins from a cell sample are routine procedures well-known to persons skilled in the art.

Once a sample of mRNA (or the corresponding cDNA) or of protein is obtained, PlGF expression, either in terms of mRNA (i.e., in all the mRNA or cDNA present in the sample), or in terms of proteins (i.e., in all the proteins present in the sample), can be measured. The method used to accomplish this depends on the type of transformation (mRNA, cDNA or protein) and on the type of sample available.

When PlGF expression is measured in terms of mRNA (or the corresponding cDNA), any technology commonly used by persons skilled in the art may be used. These technologies for analysing gene expression levels, for instance transcriptome analysis, include well-known methods such as the polymerase chain reaction (PCR, if starting with DNA), reverse transcription-PCR (RT-PCR, if starting with RNA) and quantitative RT-PCR, or nucleic acid arrays (including DNA arrays and oligonucleotide arrays) for a higher throughput.

The term "nucleic acid arrays", as used herein, means several different nucleic acid probes attached to a substrate, which may be a microarray, a glass slide, or a microsphere-size bead. The microarray may be composed of polymers, plastics, resins, polysaccharides, silica or a material containing silica, carbon, metals, inorganic glass or nitrocellulose.

The probes may be nucleic acids such as cDNA (cDNA arrays), mRNA (mRNA arrays) or oligonucleotides (oligonucleotide arrays), said oligonucleotides typically having a length of between roughly 25 and 60 nucleotides.

To determine the expression profile of a particular gene, a nucleic acid corresponding to all or part of said gene is labelled and then contacted with the array under hybridisation conditions, leading to the formation of complexes between said labelled target nucleic acid and probes complementary to this nucleic acid attached to the surface of the array. The presence of the labelled hybrid complexes is then detected.

These technologies make it possible to monitor the expression level of one gene in particular or of several genes, and even of all the genes of the genome (full genome or full transcriptome) in a biological sample (cells, tissues, etc.). These technologies are used routinely by persons skilled in the art and thus it is not necessary to detail them herein. Examples of implementations of the invention based on analysis of gene expression (cDNA arrays) and on quantitative PCR are described in the experimental section.

Alternatively, it is possible to use any current or future technology making it possible to determine gene expression on the basis of the amount of mRNA in the sample. For example, persons skilled in the art can measure gene expression by hybridisation with a labelled nucleic acid probe, such as, for example, with a Northern blot (for mRNA) or a Southern blot (for cDNA), but also by techniques such as the serial analysis of gene expression (SAGE) and derivatives thereof, such as LongSAGE, SuperSAGE, DeepSAGE, etc. It is also possible to use tissue microarrays (TMAs). The tests commonly employed with tissue arrays include immunohistochemistry and fluorescence in situ hybridisation. For the analysis of mRNA levels, tissue arrays may be coupled with fluorescence in situ hybridisation. Finally, it is possible to use massively parallel sequencing to determine the amount of mRNA in the sample (RNA-Seq, or whole-transcriptome shotgun sequencing). To that end, several methods of massively parallel sequencing are available. Such methods are described, for example, in U.S. Pat. No. 4,882,127, U.S. Pat. No. 4,849,077; U.S. Pat. No. 7,556,922; U.S. Pat. No. 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure and Ji, *Nat Biotechnol.*, 26(10): 1135-45. 2008; Pihlak et al., *Nat Biotechnol.*, 26(6): 676-684, 2008; Fuller et al., *Natural Biotechnol.*, 27(11): 1013-1023, 2009; Mardis, *Genome Med.*, 1(4): 40, 2009; Metzker, *Natural Rev. Genet.*, 11(1): 31-46, 2010.

When the expression of the marker is measured in terms of protein, it is possible to employ specific antibodies, in particular in well-known technologies such as immunoprecipitation, immunohistology, Western blot, dot blot, ELISA or ELISPOT, immunological tests using electrochemiluminescence (ECLIA), protein arrays, antibody arrays, or tissue arrays coupled with immunohistochemistry. Other techniques that may be used include FRET or BRET techniques, microscopy or histochemistry methods, notably including confocal microscopy and electron microscopy methods, methods based on the use one or more excitation wavelengths and a suitable optical method, such as an electrochemical method (voltammetry and amperometry techniques), atomic force microscopy, and radio frequency methods, such as multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, etc.), flow cytometry, radioisotope or magnetic resonance imaging, analysis by polyacrylamide gel electrophoresis (SDS-PAGE), HPLC-mass spectrophotometry and liquid chromatography-mass spectrophotometry/mass spectrometry (LC-MS/MS). All these techniques are well-known to persons skilled in the art and it is not necessary to detail them herein.

Preferably, PlGF expression is measured in terms of protein. More preferably, PlGF expression is measured using a test employing specific antibodies recognising said biomarker, in particular in well-known technologies such as immunoprecipitation, immunohistology, electrochemiluminescence (ECLIA), Western blot, dot blot, ELISA or ELISPOT, protein arrays, antibody arrays, or tissue arrays coupled with immunohistochemistry. Antibodies against PlGF are available commercially (see for example, R&D Systems, Santa Cruz, Abcam, etc.) and may be used in the methods of the invention. Even more preferably, PlGF expression is measured by Western blot or ELISA.

In a preferential embodiment of the invention, it may be useful to compare the PlGF level obtained in step a) of the method with a reference level.

The phrase "reference expression level of a biological marker", within the meaning of the present application, means any expression level of said marker used as reference. For example, a reference expression level may be obtained by measuring the expression level of the marker of interest in a biological sample from a healthy subject, for example a placenta from a healthy subject, i.e., a subject not exposed to alcohol in utero. In this case, a PlGF level from step a) lower than the reference level indicates an FASD. In particular, the inventors showed that a PlGF level lower than that of a healthy subject indicates a defective brain vascular organisation.

According to an advantageous embodiment of the present invention, the expression of the candidate marker is normalised relative to the expression of a control marker. A "control marker" according to the present invention is a marker the expression of which is identical regardless of the cell type concerned and the donor's age. According to a particular embodiment, when the candidate biomarker is a genetic marker or a protein marker, the control marker is a gene that is expressed in all cell types, independently of the subject's age, or the protein product thereof. In a more particular embodiment, said control marker is a housekeeping gene or the protein product of said housekeeping gene. A housekeeping gene is a gene that is expressed in all cell types and that provides a basic function necessary for cell survival. A list of human housekeeping genes can be found, for example, in Eisenberg et al., (*Trends in Genetics* 19:362-365, 2003). A preferred housekeeping gene according to the invention is a gene selected from the group consisting of B2M, TFRC, YWHAZ, RPLO, 18S, GUSB, UBC, TBP, GAPDH, PPIA, POLR2A, ACTB, PGK1, HPRT1, IPO8 and HMBS.

The method of the invention is particularly useful because it makes it possible to make a noninvasive diagnosis from an early age. Children diagnosed as having suffered brain damage following uterine alcohol exposure may thus be provided early and rapid care. It has been shown that early care leads to better functional and cognitive recovery (Toutain et al., Psychotropes, 13: 49-68, 2007).

According to another aspect, the invention has as an object a method for treating foetal alcohol spectrum disorders in a subject. Said method comprises the following steps:
a) diagnosing FASDs in said subject by any one of the methods above; and
b) treating said subject if step a) concludes that said subject has FASDs.

The term "treatment", as used herein, means any action making it possible to decrease or eradicate the symptoms or the cause of FASDs. A treatment within the meaning of the invention may comprise administering a pharmacological substance and/or psychotherapeutic treatment.

The invention will be described more precisely by means of the examples below. Said examples are provided herein by way of illustration and are not, unless otherwise specified, intended to be limiting.

G, H: Immunohistochemical staining showing the VEGF-R2 (G) distribution in placental syncytiotrophoblast layers labelled with Glut-1 (H). Nuclei were stained with Hoechst. *p<0.05 vs the "Control" group using an unpaired t-test.

Figure 6:
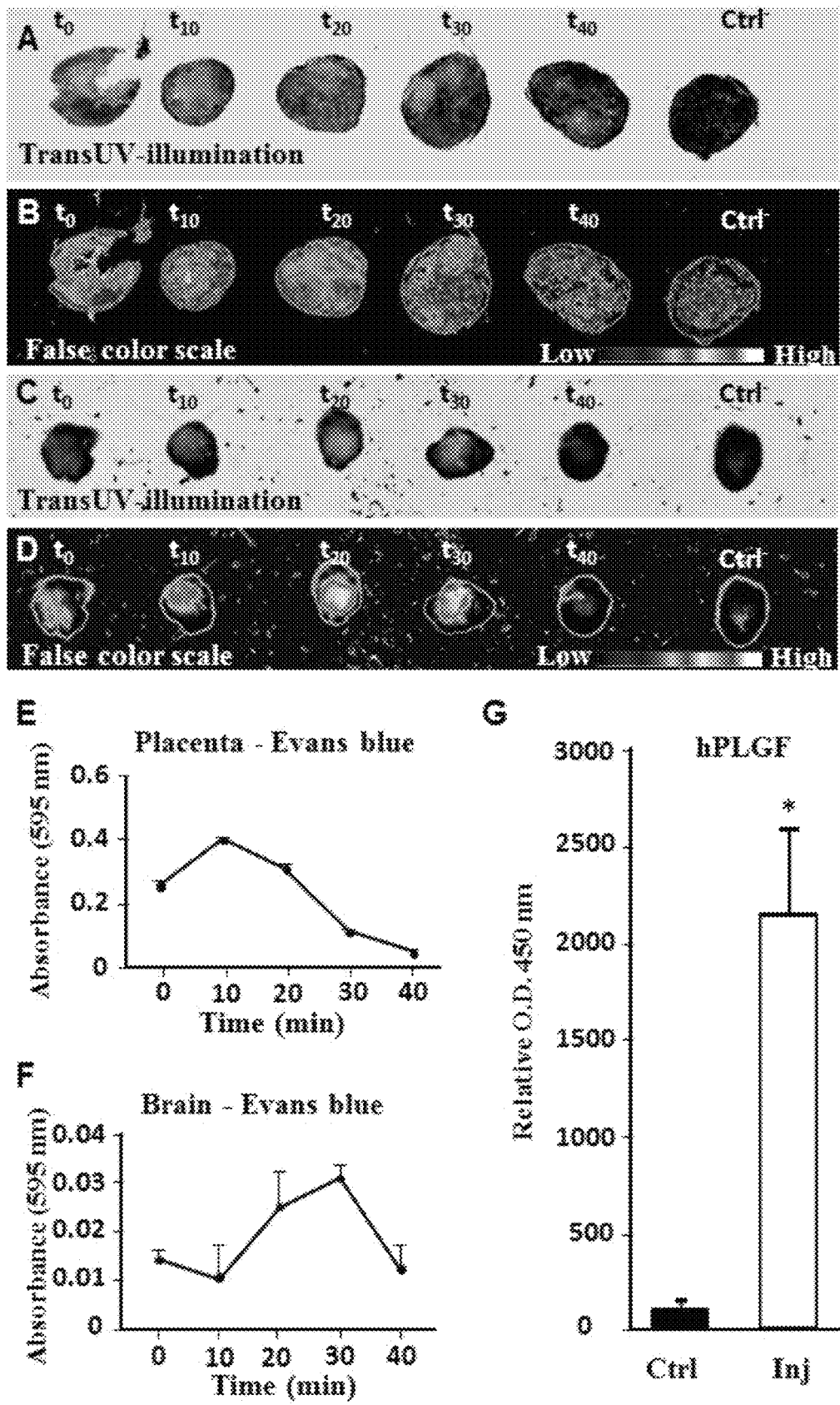

FIG. 6. Diffusion of Evans blue injected in utero from the placenta to the foetal brain. A, B: Time-course visualisation of Evans blue administered by microinjection into the placenta of pregnant mice at GD15. Fluorescence was detected by UV illumination (A) and is represented using a false-colour scale (B). C, D: Time-course visualisation of Evans blue fluorescence in the foetal brain after placental microinjection at GD15. Fluorescence was detected by UV illumination (C) and is represented using a false-colour scale (D). E, F: Time-course quantification by spectrophotometry of absorbance at 595 nm of the signal of the injected Evans blue in the placentas (E) and subsequently in the brains of the corresponding foetuses (F). G: ELISA quantification of human PlGF in foetal mouse brain 30 min after injection of hPlGF in the placentas of pregnant mice at GD15. *p<0.05 vs the "Control" group using an unpaired t-test.

Figure 7:
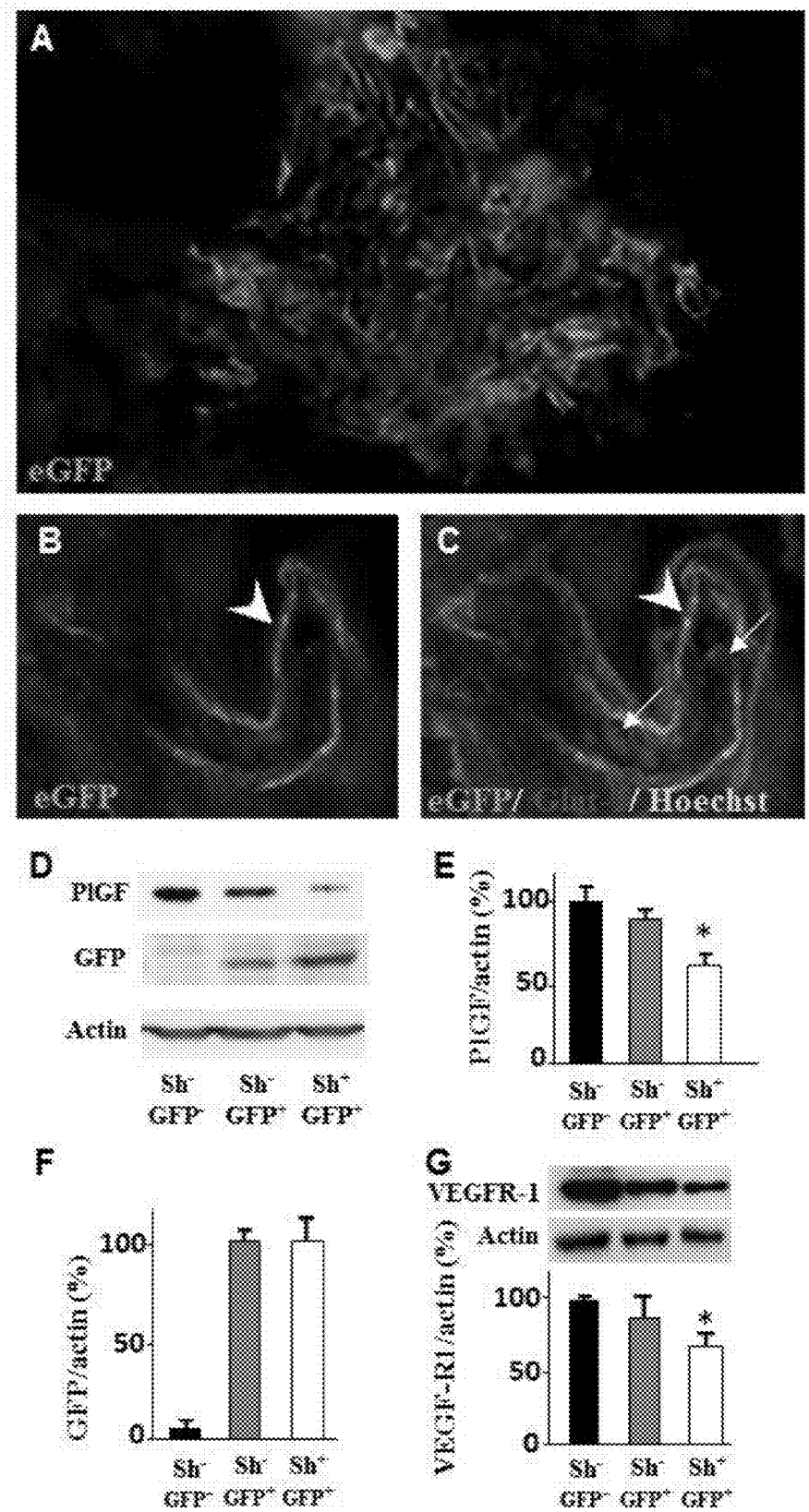

FIG. 7: Effect of repression of placental PlGF by in utero transfection on brain VEGF-R1 levels. A: Microphotography showing eGFP expression 48 hours after in utero transfection of a plasmid encoding eGFP in placentas of pregnant mice at GD15. B, C: Triple staining eGFP/Glut-1/Hoechst showing that eGFP fluorescence (B) is mainly associated with the foetal trophoblast layer labelled with Glut-1 (C; arrowheads). The maternal trophoblast layer, also labelled with Glut-1, is not transfected. The foetal trophoblast layer is identified by the presence of nucleated red blood cells characteristic of foetal circulation (arrow). D: Visualisation by Western blot of PlGF, GFP and actin proteins in the placentas of non-transfected (Sh$^-$/GFP$^-$), GFP-transfected (Sh$^-$/GFP$^+$) and shPlGF/GFP-transfected (Sh$^+$/GFP$^+$) animals. E, F: Quantification by Western blot of PlGF (E) and GFP (F) expression levels in the placentas of non-transfected (Sh$^-$/GFP$^-$), GFP-transfected (Sh$^-$/GFP$^+$) and shPlGF/GFP-transfected (Sh$^+$/GFP$^+$) animals. G: Quantification by Western blot of VEGF-R1 expression levels in the foetal brain from non-transfected (Sh$^-$/GFP$^-$), GFP-transfected (Sh$^-$/GFP$^+$) and shPlGF/GFP-transfected (Sh$^+$/GFP$^+$) placentas. *p<0.05 vs the "Sh$^-$/GFP$^-$" group using ANOVA followed by Tukey's HSD multiple comparison test.

Figure 8:
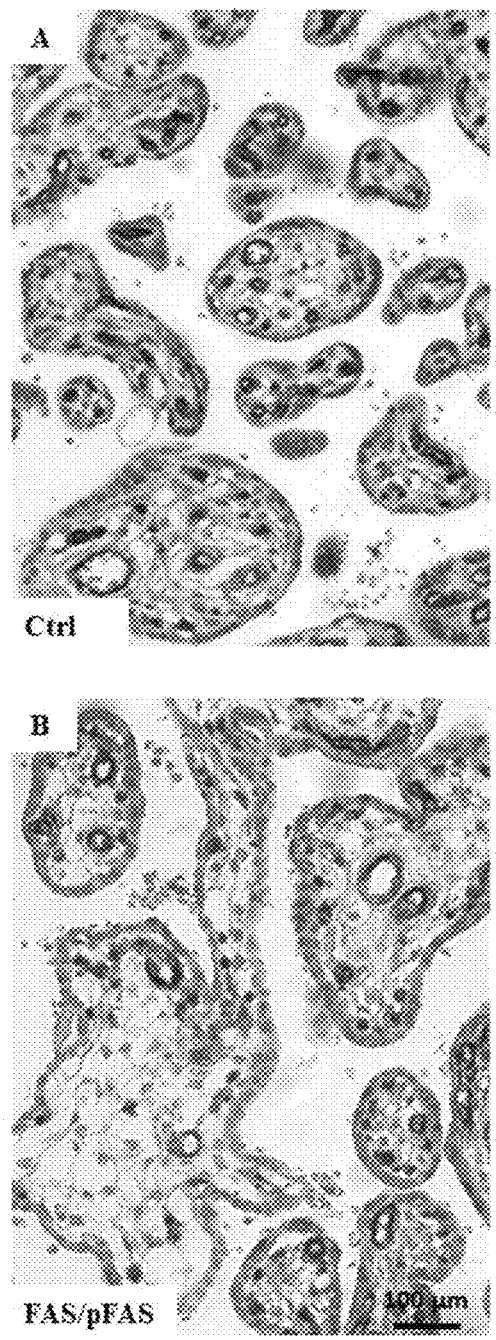
Figure 8:
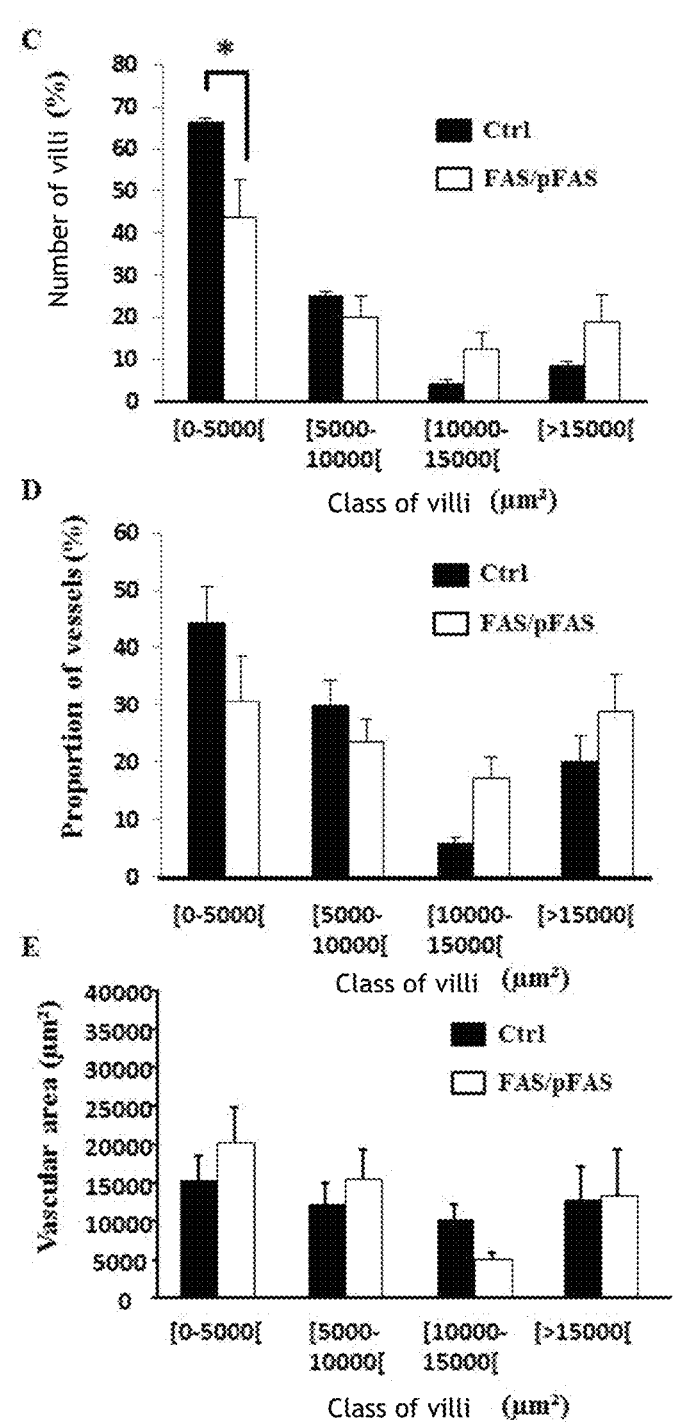

FIG. 8. Morphometric characterisation of the effects of in utero alcohol exposure on gestational week 20 to 25 human placenta. A, B: Anti-CD31 immunohistochemical staining and toluidine blue counterstaining to visualise the microvessels (brown) present in the placental villi (blue) of the "Control" (A) and "FAS/pFAS" (B) groups at 20 to <25 weeks of gestation (WG). C: Percentage of villi classified by size in placentas of the "Control" and "FAS/pFAS" groups at 20 to <25 WG. D: Vessel distribution by villus size in placentas of the "Control" and "FAS/pFAS" groups at 20 to <25 WG. E: Vascular surface area by villus size in placentas of the "Control" and "FAS/pFAS" groups at 20 to <25 WG. *p<0.05 vs the "Control" group using an unpaired t-test.

Figure 9:
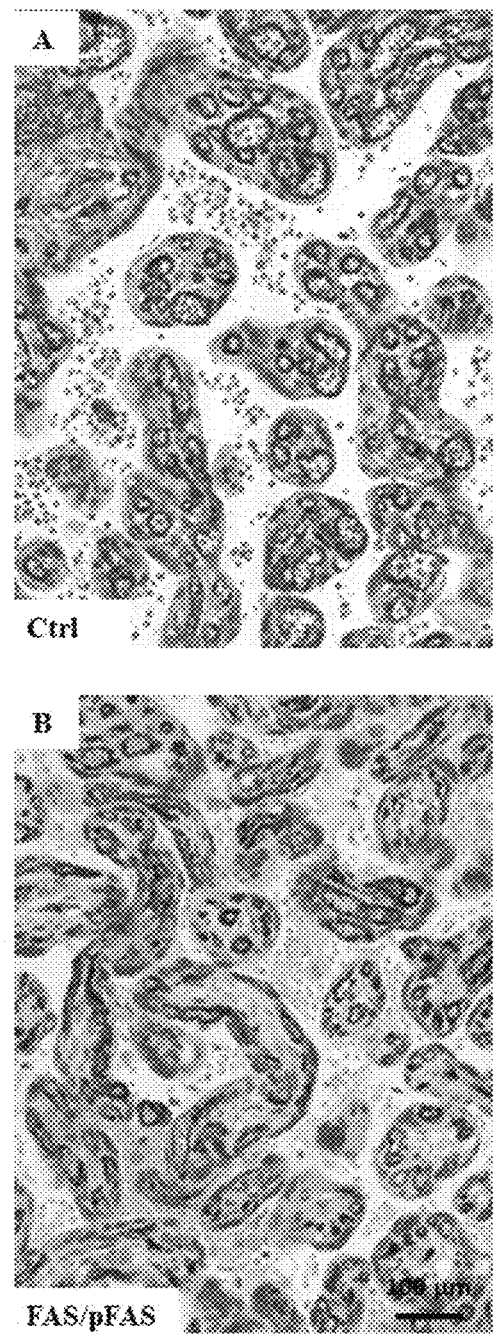
Figure 9:
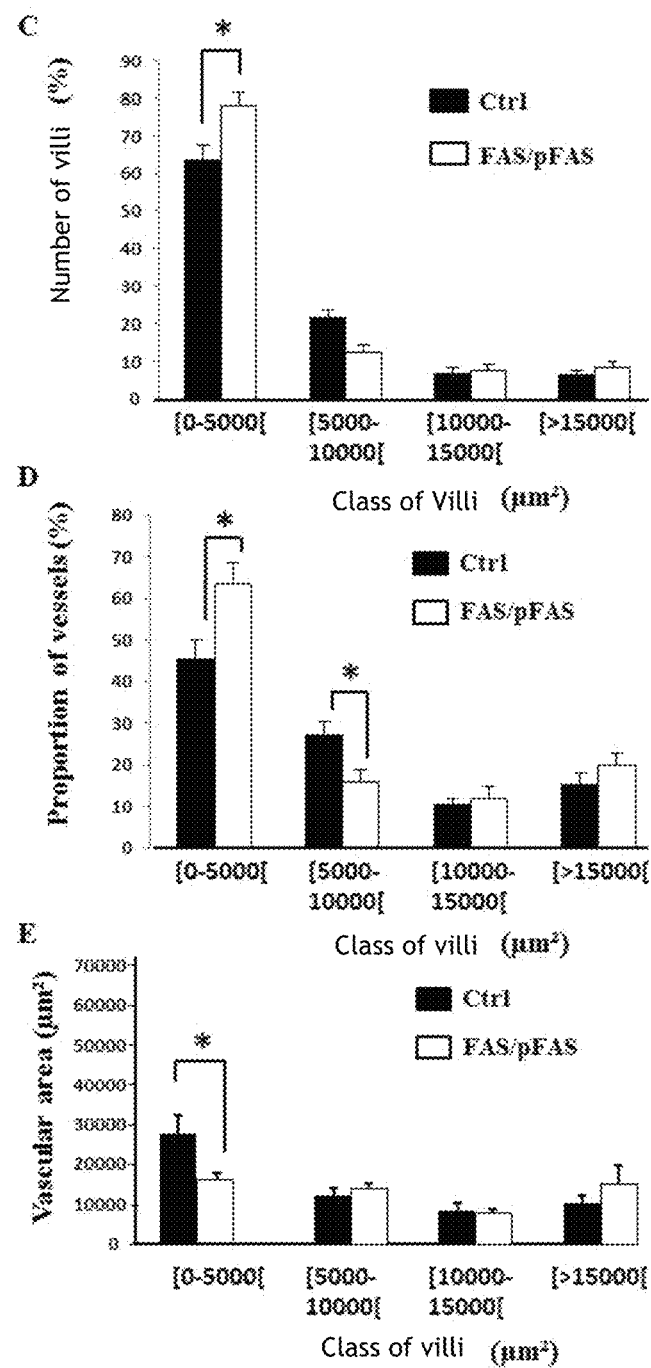

FIG. 9. Morphometric characterisation of the effects of in utero alcohol exposure on gestational week 25 to 35 human placenta. A, B: Anti-CD31 immunohistochemical staining and toluidine blue staining to visualise the microvessels (brown) present in the placental villi (blue) of the "Control" (A) and "FAS/pFAS" (B) groups at 25 to <35 WG. C: Percentage of villi classified by size in placentas of the "Control" and "FAS/pFAS" groups at 25 to <35 WG. D: Vessel distribution by villus size in placentas of the "Control" and "FAS/pFAS" groups at 25 to <35 WG. E: Vascular surface area by villus size in placentas of the "Control" and "FAS/pFAS" groups at 25 to <35 WG. *p<0.05 vs the "Control" group using an unpaired t-test.

Figure 10:
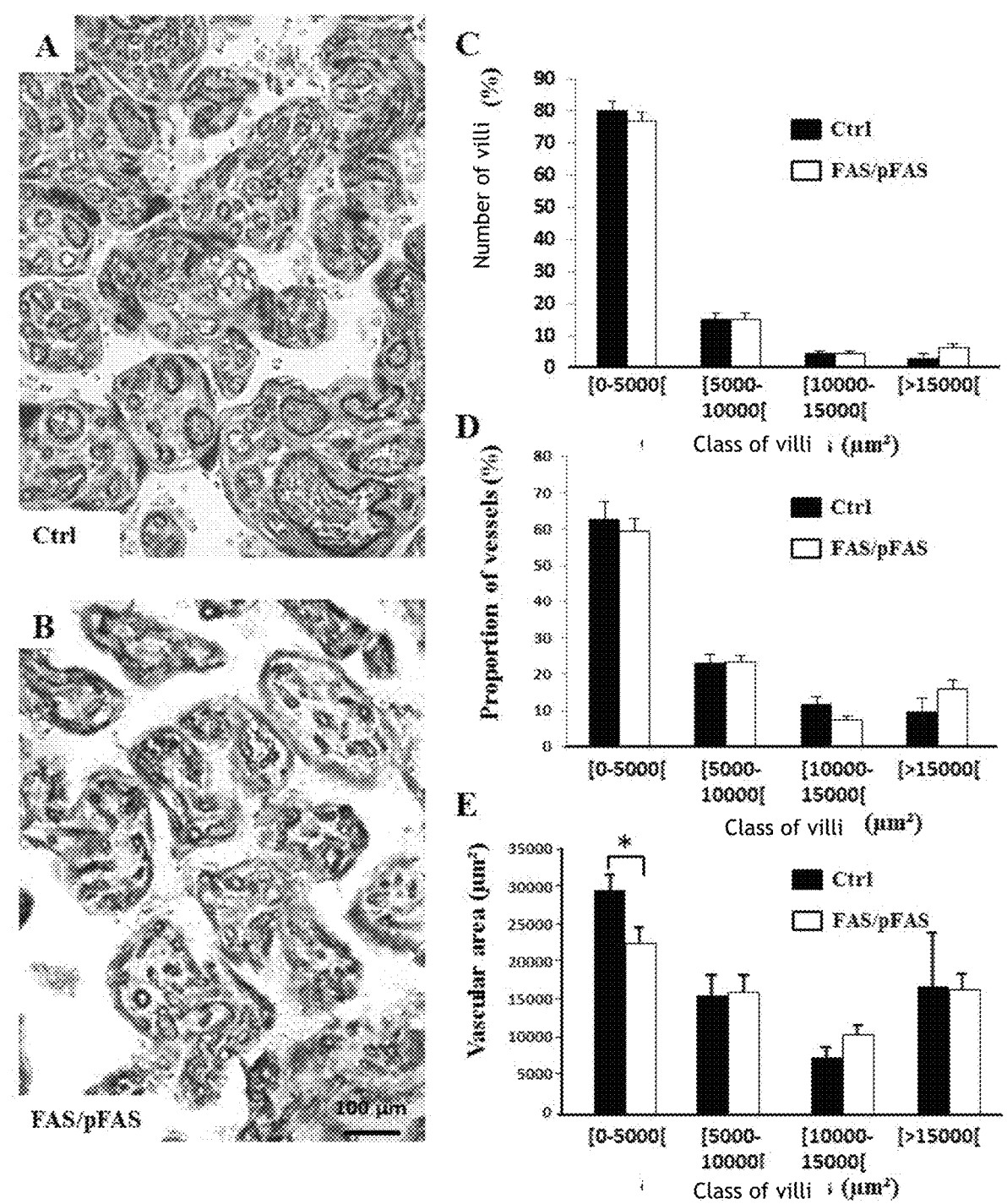

FIG. 10. Morphometric characterisation of the effects of in utero alcohol exposure on gestational week 35 to 42 human placenta. A, B: Anti-CD31 immunohistochemical staining and toluidine blue staining to visualise the microvessels (brown) present in the placental villi (blue) of the "Control" (A) and "FAS/pFAS" (B) groups at 35 to <42 WG. The microvessel lumen area is greatly reduced in the "FAS/pFAS" group. C: Percentage of villi classified by size in placentas of the "Control" and "FAS/pFAS" groups at 35 to <42 WG. D: Vessel distribution by villus size in placentas of the "Control" and "FAS/pFAS" groups at 35 to <42 WG. E: Vascular surface area by villus size in placentas of the "Control" and "FAS/pFAS" groups at 35 to <42 WG. *p<0.05 vs the "Control" group using an unpaired t-test.

Figure 11:
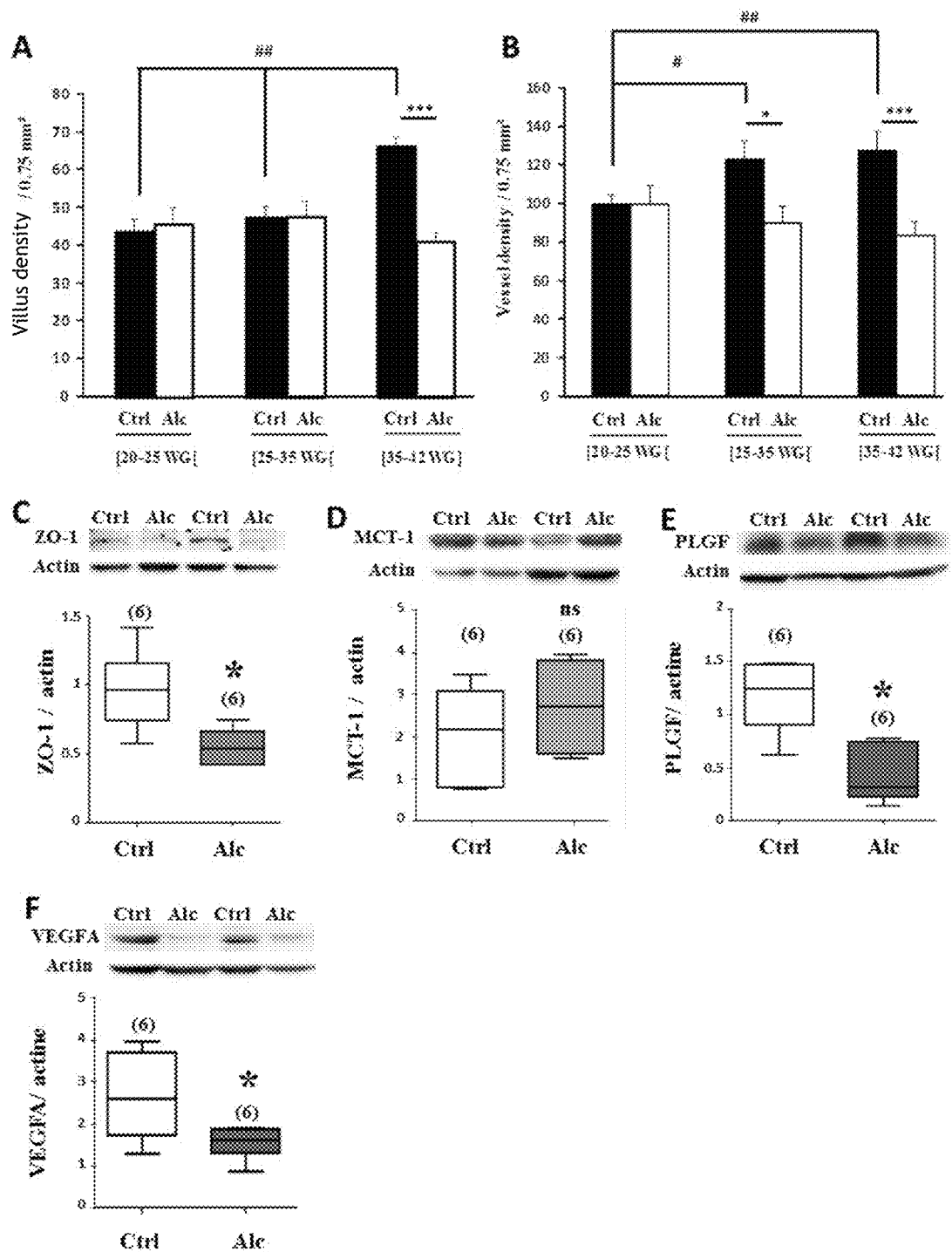

FIG. 11. Time-course effects of in utero alcohol exposure on villus and vessel densities in human placentas and Western blot characterisation of pro-angiogenic proteins and energy metabolism. A: Changes in villus densities in placentas of the "Control" (A) and "FAS/pFAS" (B) groups at 20 to <25 WG, 25 to <35 WG, and 35 to <42 WG. B: Changes in vessel densities in placentas of the "Control" and "FAS/pFAS" groups at 20 to <25 WG, 25 to <35 WG, and 35 to <42 WG. $^\#$p<0.05, $^{\#\#}$p<0.01 vs the "Control" group as indicated on the graph. *p<0.05, ***p<0.001 for the "Control" vs "Alcohol" groups for a given gestational age group. C-H: Quantification by Western blot of ZO-1 (C), MCT-1 (D), PlGF (E), VEGF-A (F), VEGF-R1 (G) and VEGF-R2 (H) protein levels in placentas of the "Control" and "FAS/pFAS" groups. *p<0.05 vs the "Control" group using an unpaired t-test.

Figure 12:
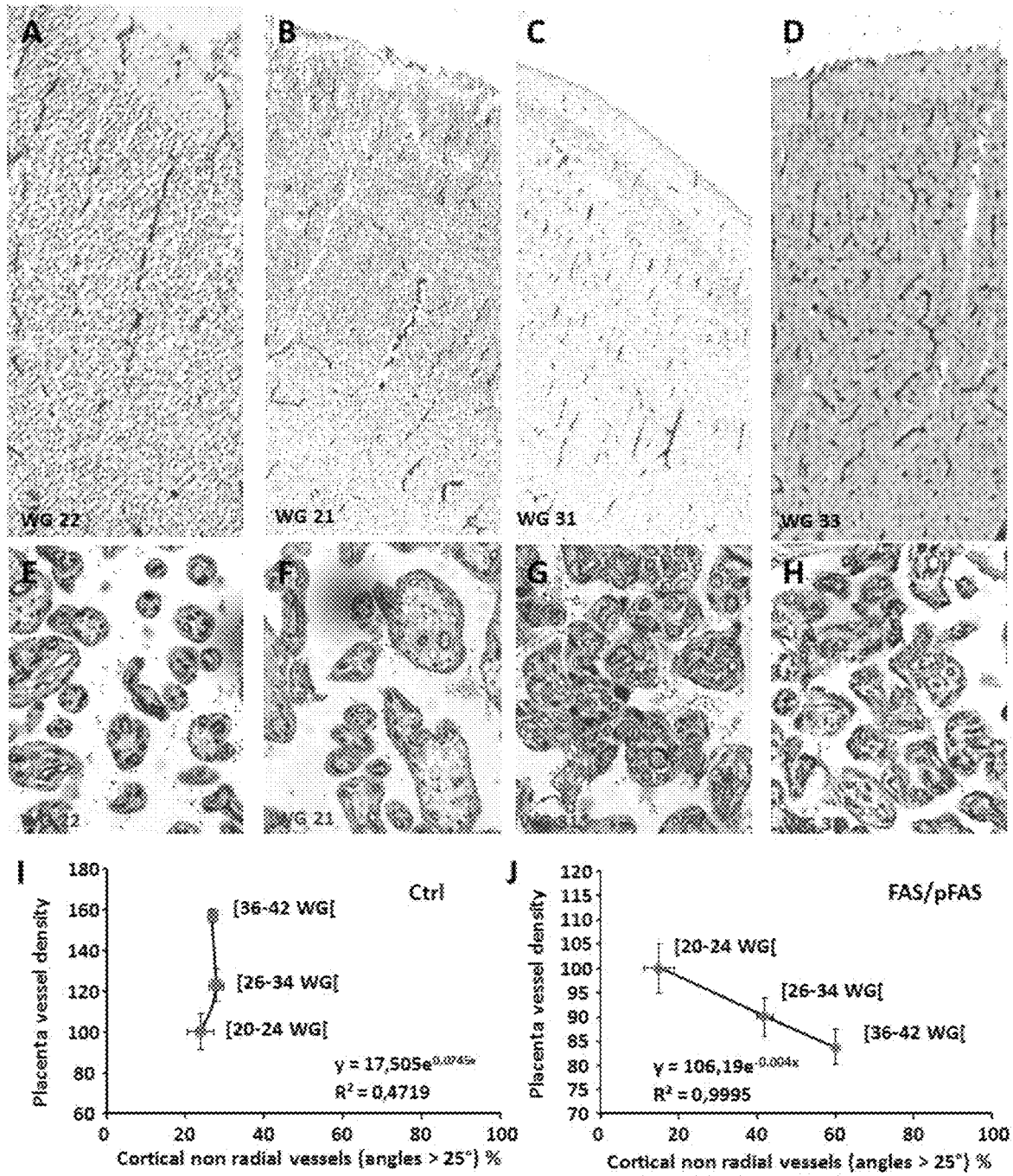

FIG. 12. Comparison of cerebral and placental damage observed in human foetuses and induced by in utero alcohol exposure and statistical correlation. A-H: Vascular organisation in the brains (A, D) and the placentas (E, H) of patients of the "Control" group at 22 WG (A, E) and 31 WG (C, G) and vascular organisation in the brains (B, D) and the placentas (F, H) of patients of the "FAS/pFAS" group at 21 WG (B, F) and 33 WG (D, H). I, J: Statistical correlation between cortical vascular disorganisation and placental vascular density in patients of the "Control" (I) and FAS/pFAS (J) groups.

EXAMPLES

Brain Angiogenesis Abnormalities Following In Utero Alcohol Exposure

Effects of In Utero Alcohol Exposure on Brain Vasculature Development

Figure 1:
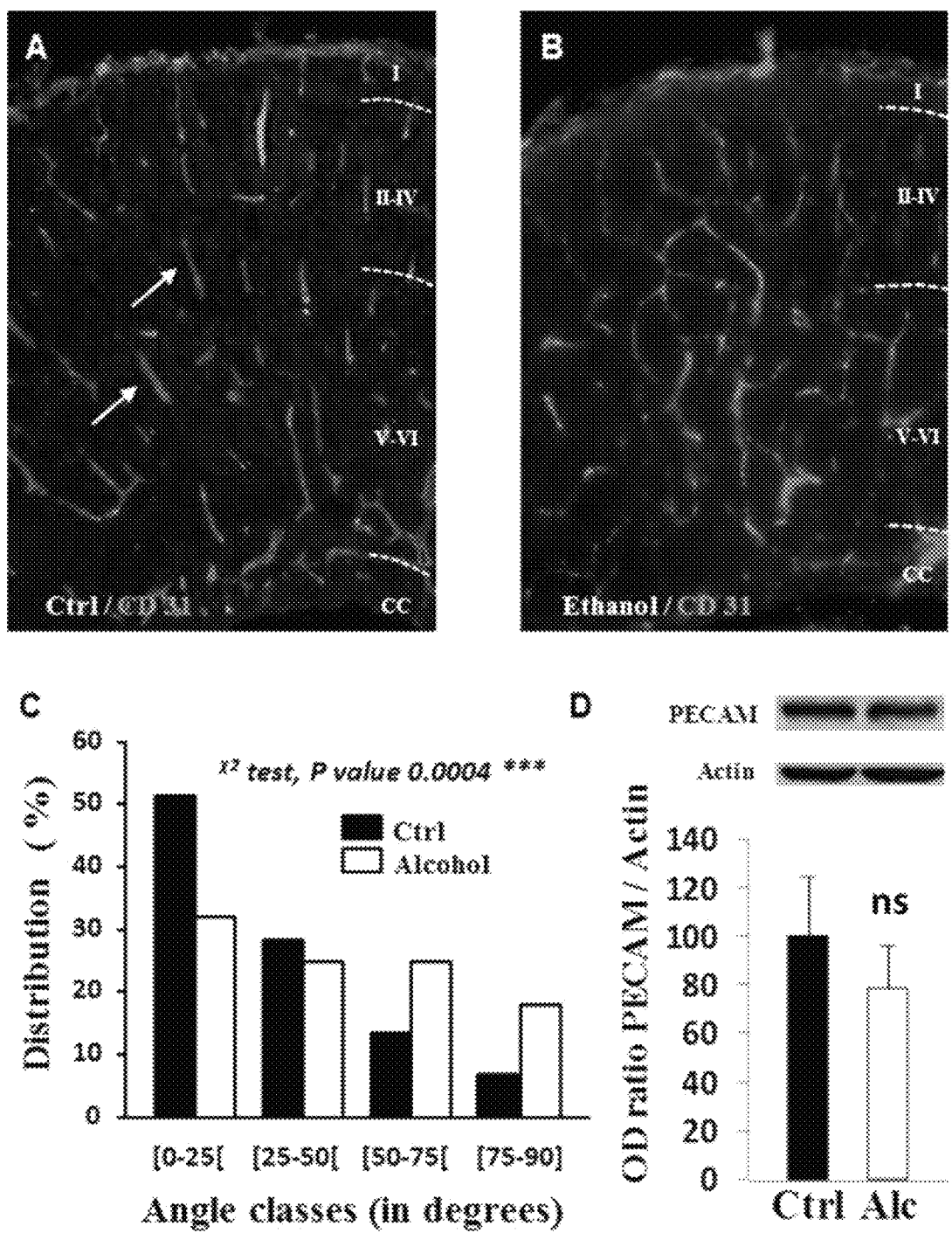
FIG. 1. Effects of in utero alcohol exposure on cortical angiogenesis in E20 mouse embryos. A, B: Effects of foetal alcohol exposure from GD15 to GD20 on cortical microvessel organisation in control animals (A) and in alcohol-exposed animals (B). Brain microvessels were visualised using anti-CD31 immunohistochemistry. The arrows indicate brain microvessels with a radial orientation in the "Control" group. Note a loss of the radial organisation in the "Alcohol" group. I-VI: Cortical layers; CC: Corpus callosum. C: Distribution of the orientation (angle classes) of cortical microvessels in the immature cortex of GD20 foetuses. Statistical analysis was performed using the $x^2$ test. D: Quantification by Western blot of the effects of foetal alcohol exposure during the last week of gestation on the cortical expression of CD31 at GD20. ns vs the "Control" group using an unpaired t-test.

The present inventors previously showed that prenatal alcohol exposure induces brain vascular disorganisation. In particular, the effect of alcohol is associated with a significant decrease in the number of cortical vessels with a radial orientation and an increase in the number of microvessels with a random orientation (FIG. 1). In parallel with the study carried out in mice, analysis of brain microvasculature in humans showed that, as in mice, the cortical microvessels that have a radial orientation in the "Control" group are completely disorganised in the "FAS/pFAS" group (FIG. 12 and Jegou et al., 2012).

Figure 2:
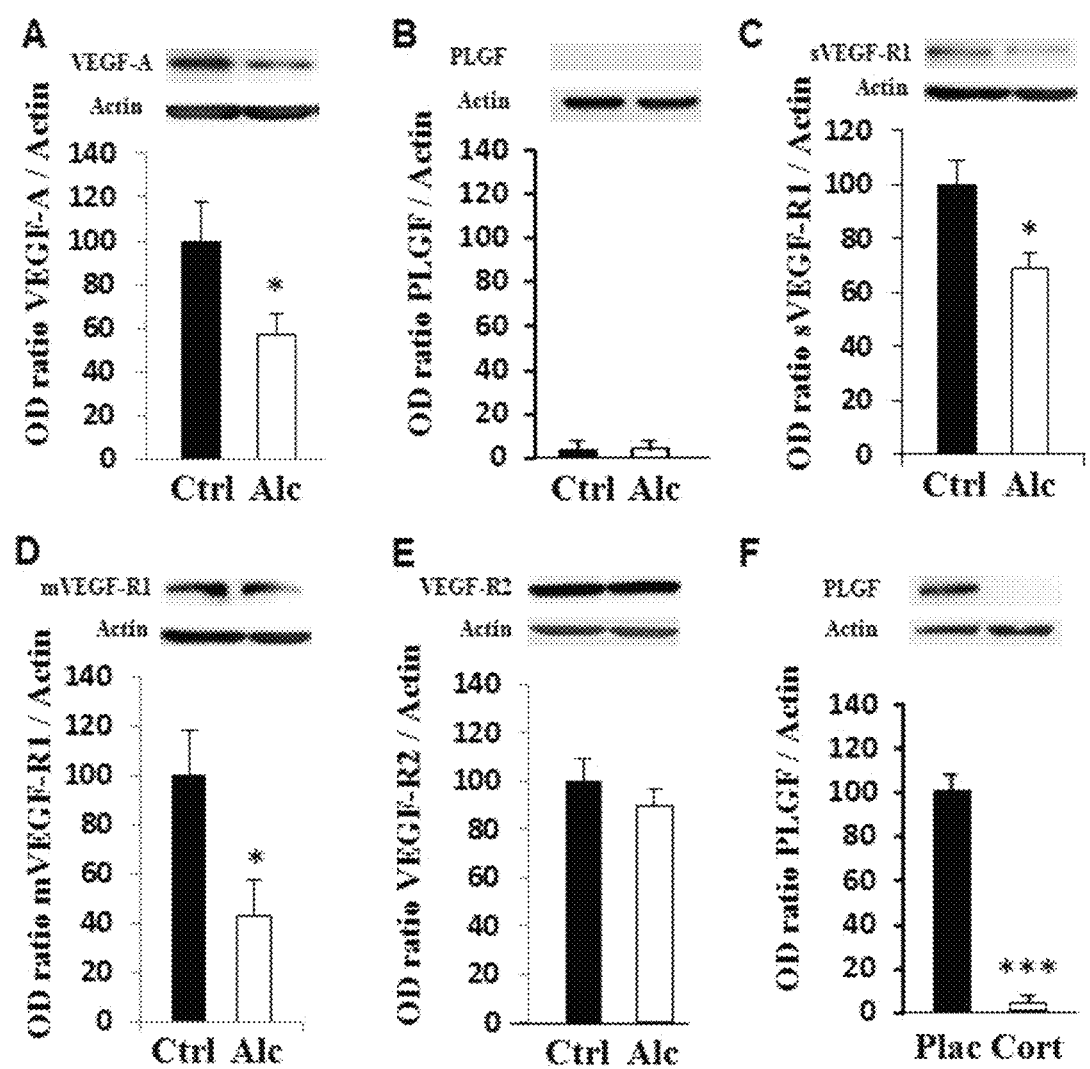
FIG. 2. Effects of in utero alcohol exposure on the expression of VEGF/PlGF family members in E20 mouse embryos. A-E: Quantification by Western blot of VEGF-A (A), PlGF (B), sVEGF-R1 (C), mVEGF-R1 (D) and VEGF-R2 protein levels in the cortex of the "Control" and "Alcohol" groups. F: Comparison by Western blot of PlGF protein levels in the cortex and the placenta of E20 embryos of the "Control" group. ***p<0.001 vs the "Control" group using an unpaired t-test.

Effects of In Utero Alcohol Exposure on the Expression of Genes Representative of the Vasculature in Mice Quantitative RT-PCR (mRNA) and Western blot (protein) studies revealed a marked dysregulation of the levels of VEGF-R1 and VEGF-R2 receptors which relay the pro-angiogenic effects of factors such as VEGF-A or PlGF. Brain vasculature abnormalities are thus associated with a dysregulation of the expression of brain pro-angiogenic receptors (FIG. 2 and Jegou et al., 2012).

Abnormalities of Placental Angiogenesis Following In Utero Alcohol Exposure

Figure 3:
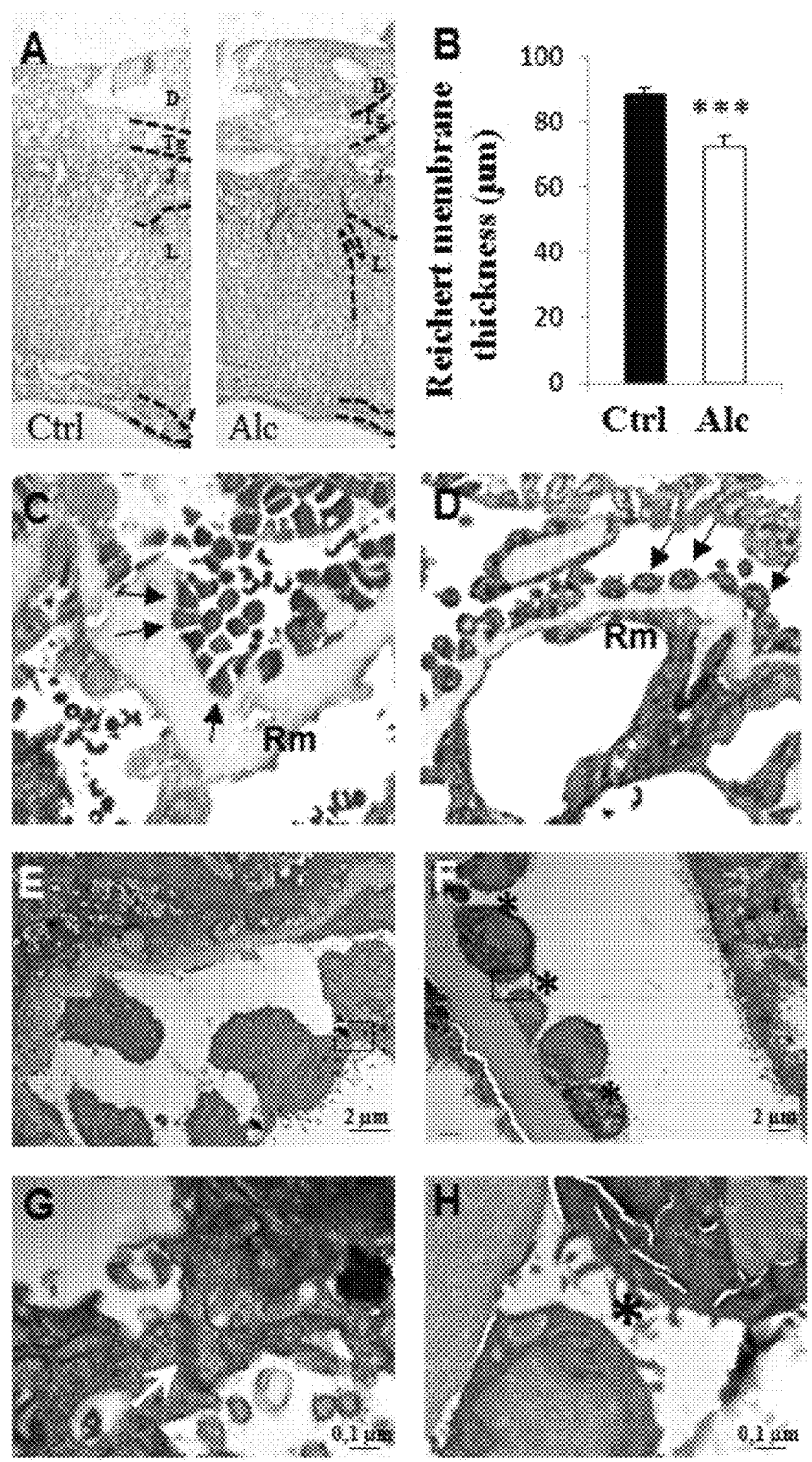
FIG. 3. Effects of in utero alcohol exposure on the ultrastructural features of the placenta in GD20 mice. A: Observation by cresyl violet staining of the effect of alcohol exposure on the laminar structure of the placenta. The maternal side of the placenta is pointing up. Alcohol affects segregation of the junctional and labyrinth zones (dotted lines). B: Quantification by image analysis of the effects of alcohol on Reichert's membrane thickness. C, D: Observation at low magnification of the giant trophoblast layer in the "Control" (C) and "Alcohol" (D) groups. Giant trophoblasts are indicated by arrows. They have a typical rectangular shape in the placenta of the "Control" group, whereas in the "Alcohol" group they have a round shape. E-H: Images acquired by electron microscopy at medium (E, F) and high (G, H) magnification showing the cell morphology of giant trophoblasts and the presence of tight junctions (arrows) in the "Control" (E, G) and "Alcohol" (F, H) groups. Tight junctions (stars) are no longer visible in the alcohol-treated animals. The insets in E and F indicate the zone observed at higher magnification in G and H, respectively. D: maternal decidua; J: junctional zone; L: labyrinth zone; Tg: giant trophoblast layer. ***p<0.001 vs the "Control" group using an unpaired t-test.

Various placental parameters were studied in mice (FIGS. 3-5) and in humans (FIGS. 8-10) by an immunohistochemical approach coupled with morphometric analysis comprising in particular placental villus density and size, vascular density and surface area, and proportion of vessels per villus. In humans, these parameters were measured and compared between 34 placentas from control individuals and 36 placentas from individuals exposed to alcohol in utero. The placentas were divided into three age groups comparable with those of the brain study (Jegou et al., 2012). The results concerning the age groups 20 to <25 WG, 25 to <35 WG, and 35 to <42 WG are presented in this document.

In particular, morphometric analysis indicates that the distribution of placental vessels by villus size and the vascular surface area are significantly affected by alcohol exposure (FIG. 11). Moreover, longitudinal analysis of vascular density, taking into account the "age" factor, indicates that in the "Controls" group placental angiogenesis strongly increases between the age groups 20 to <25 WG and 25 to <35 WG. This high placental vascularization is explained by significant brain development during the third trimester of pregnancy requiring increased oxygen and nutrients. On the other hand, foetal alcohol induces a stagnation or a lowering of placental vascular density (FIG. 11).

In conclusion, the present results indicate that there exists in the human placenta, as in the cerebral cortex, vascular abnormalities in the alcohol-exposed subjects. These results thus support the hypothesis of a correlate between brain disorders and impaired placental angiogenesis.

Demonstration of a Correlation Between Placental and Brain Vascular Abnormalities The placental and brain vascular abnormalities observed in humans following in utero alcohol exposure may be the result of completely independent processes with no cause and effect relationship or, conversely, may be closely interlinked. The fact that the source of PlGF is unique and of placental origin speaks in favour of the second hypothesis. However, in order to show a link between cerebral and placental vascular defects, we carried out a correlation study in subjects of the "Control" group and another in individuals of the "FAS/pFAS" group (FIG. 12).

The results show that in the "Control" group, the increase in placental vascularization does not affect the radial organisation of the cortical vessels ($R^2$ 0.4719). On the other hand, the lack of placental vascularization observed in the "FAS/pFAS" group is closely correlated with the random orientation of the cortical vessels ($R^2$ 0.9995). There is thus a highly significant interaction between placental and brain vascular alterations.

Demonstration of a Functional Link Between Placental PlGF and the Brain Receptor Thereof In utero administration of a fluorescent molecule into the placenta of gestating (GD15) mice is found after 20-30 min in the foetal brain (FIG. 6). In addition, recombinant human PlGF injected into the placenta of mice is detected after 30 min by ELISA in the foetal brain (FIG. 6). These data indicate that placental molecules, and in particular PlGF, are able to reach the foetal brain.

Invalidation by in utero placenta transfection for murine PlGF by shRNA results in a repression of placental PlGF protein levels after 48 hours (FIG. 7). This effect is associated at the cerebral level by a decrease in VEGF-R1 receptor protein levels (FIG. 7). These results indicate that i) the specific repression of placental PlGF directly effects the expression of the brain receptor, ii) the specific repression of placental PlGF mimics the effects of alcohol on brain VEGF-R1 expression (FIGS. 2 and 7).

Identification of the Placental Factors that are Biomarkers of Brain Damage

The correlation study above shows for the first time that the placental vascular defects induced by foetal alcohol exposure are directly linked with brain vascular defects. Consequently, placental factors whose role in angiogenesis is proven become candidate biomarkers of brain vascular defects.

Expression levels of proteins known to be either factors of angiogenesis or specific proteins of the vasculature were quantified by Western blot. This work was carried out in animals (mice; placenta/brain) and in humans (placenta).

Figure 4:
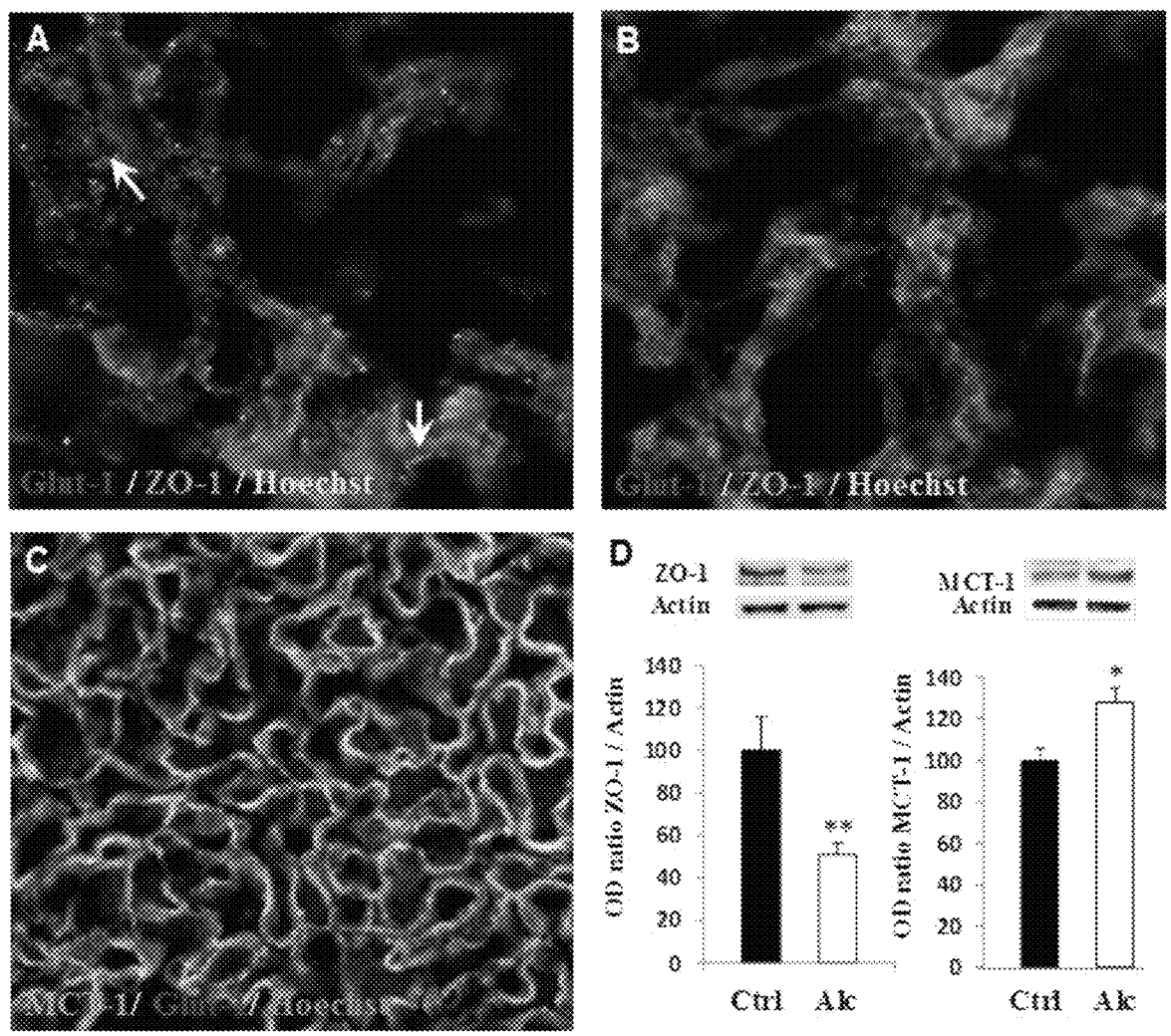
FIG. 4. Effects of in utero alcohol exposure on the expression of proteins involved in the placental barrier and in placental energy metabolism. A, B: Immunohistochemical observation of ZO-1 protein in the placental labyrinth zone of mice of the "Control" (A) and "Alcohol" (B) groups. ZO-1 protein appears as forming groups of dots (arrows) in the "Control" group whereas staining is diffuse in the "Alcohol" group. The trophoblast layers were revealed by immunoreactivity with the glucose transporter Glut-1. Nuclei were stained with Hoechst. C: Double staining with antibodies against monocarboxylate MCT-1 and glucose transporters in the labyrinth zone of a "Control" placenta. By contrast with Glut-1, the expression of MCT-1 is associated with the maternal layer of the syncytiotrophoblast. Nuclei were stained with Hoechst. D: Quantification by Western blot of ZO-1 and MCT-1 protein expression levels in placentas of the "Control" and "Alcohol" groups. *p<0.05, **p<0.01 vs the "Control" group using an unpaired t-test.
Figure 5:
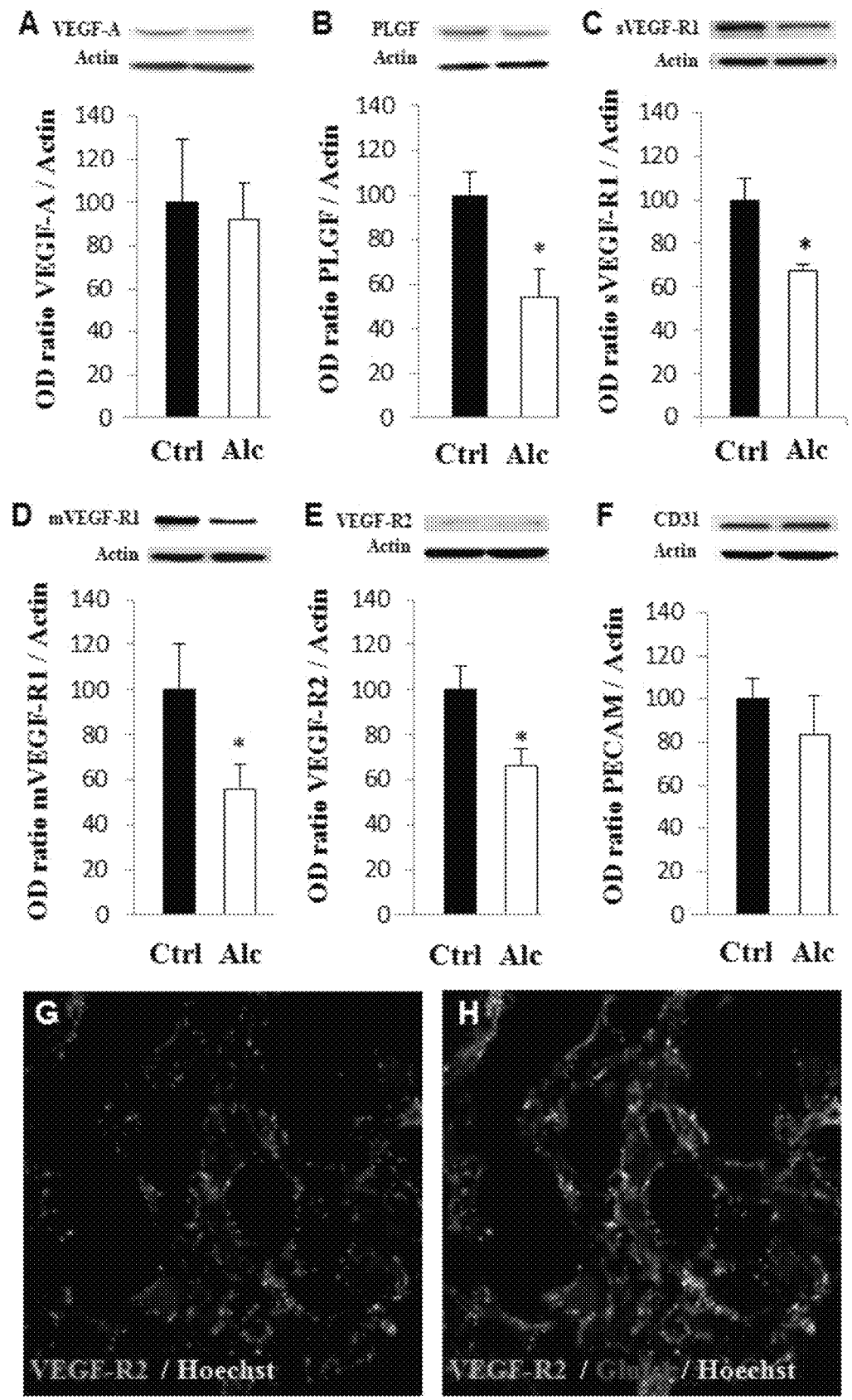
FIG. 5. Effects of in utero alcohol exposure on the expression of VEGF/PlGF family members in murine placentas. A-F: Quantification by Western blot of the effects of alcohol exposure during the last week of gestation on the placental expression of VEGF-A (A), PlGF (B), sVEGF-R1 (C), mVEGF-R1 (D), VEGF-R2 (E) and CD31 (F) at GD20.

In mice, quantification of placental VEGF-A and PlGF expression levels show a significant decrease in PlGF alone (for which the placenta is the only source in the organism; FIG. 5). In parallel, quantification of VEGF-A and PlGF receptors indicates that the expression of VEGF-R1 (the unique PlGF receptor) is decreased in both the placenta and the brain (FIGS. 2 and 5). This very marked reduction is on the order of 50%. VEGF-R2 expression in the brain, in turn, is not affected. Moreover, quantification of vascular ZO-1 protein, involved in establishing the placental and haematoencephalic barrier, is strongly decreased in the placenta (FIG. 4).

In parallel to the work carried out in mice, analysis of protein expression was carried out on human placentas for which maternal alcohol exposure was proven and the children were living. We collected 7 "Control" placentas and 6 "Alcohol" placentas and quantified by Western blot the candidate markers identified in mice. The results indicate that in the "Alcohol" group PlGF expression and ZO-1 expression are very strongly decreased as in mice (FIG. 11). These data indicate that the effects of foetal alcohol observed in the placenta and in the brain are found in two different species, mice and humans.

Evaluation of PlGF Concentrations in Umbilical Cord Blood, Placenta and Maternal Blood from Two Groups of Patients (Control vs Exposed to Alcohol In Utero)

The main objective of this clinical study is to compare PlGF concentrations in the umbilical cord and the placenta between two groups of patients and to carry out a follow-up at 2 and 6 years of the neurodevelopment of both groups of patients. In the first group, the patients were exposed to alcohol in utero. The second group is a control group of patients who were not exposed to alcohol in utero.

This clinical study has the following objectives:
comparison of PlGF concentrations in the maternal blood;
neurological clinical examination upon birth of the child;
follow-up at 2 years of age in paediatric consultation to evaluate neurodevelopment, notably via an Ages and Stages Questionnaire (ASQ), and
follow-up at 6 years of age in paediatric consultation to evaluate neurodevelopment, via a parental questionnaire and a neuropsychological assessment.

In this clinical study, 30 women who consumed alcohol during their pregnancy and 30 abstinent pregnant women (control group) are monitored. All the women monitored are at least 18 years of age and signed a consent protocol.

The documented alcohol consumption during pregnancy is chronic consumption of at least 30 g of alcohol per week or acute binge drinking-type consumption during pregnancy (with a unit of 10 g of pure alcohol corresponding to 25 cL of 4.5° beer, 10 cL of 12° wine, 3 cL of whisky, 7 cL of sherry, etc.).

In the control group, no alcohol consumption during pregnancy is documented.

Thirty patients in each group are needed to show a difference in PlGF level of 4.7 pg/dL with the power of the test being 80%.

The assaying of PlGF in the umbilical cord blood and the placenta is carried out by electrochemiluminescence immunoassay (automated ECLIA analysis of PlGF (Cobas e411 Analyzer) made available by Roche Diagnostics) on samples of cord blood and placentas (control group vs alcohol-exposed group).

Tissue samples of cord blood and placentas are taken and then frozen and stored at −80° C. Quantification on tissue extracts of blood and placental PlGF is then carried out.

A clinical examination upon discharge from maternity (weight, height, head circumference, axial and peripheral tone, reactivity, primitive reflexes, postural adaptations, facial dysmorphism suggestive of FAS, possible malformations) is carried out.

A follow-up of the children at 2 and 6 years of age is carried out by targeting cognitive development and behavioural disorders.

During the consultation at 2 years of age, weight, height and head circumference (HC) are measured. An ASQ is filled out and a neurological examination (brain MRI to investigate brain malformations) and an assessment of signs of facial dysmorphism are carried out. Investigation of vascular rigidity of the retinal vessels by an ophthalmologist is also carried out.

During the consultation at 6 years of age, weight, height and HC are measured and a neurological and neuropsychological examination using neurodevelopmental scales (WISC IV and NEPSY) is carried out. Conners parent and teacher questionnaires (for screening hyperactivity) and social communication questionnaires (SCQ) for parents (related to behaviour) are also filled out during this consultation.

In both groups, at birth, at 2 years of age and at 6 years of age, clinical examinations (behaviour, eye pursuit-fixation, axial and peripheral tone, neuromotor assessment, stretch reflexes, complete physical examination to investigate malformations) and paraclinical examinations (fundus of the eye, brain MRI, parental ASQ, WISC IV and NEPSY developmental scales, Conners and SCQ questionnaires for parents and teachers) are carried out.

The two groups of patients are compared using the Mann-Whitney nonparametric test. A significance threshold of 5% is set.

The results obtained are consistent with that which was expected.

Conclusion

In the light of the various results obtained by the inventors in mice and in humans, it appears that
i) foetal alcohol exposure affects brain angiogenesis and the organisation of the brain vasculature,
ii) these brain alterations are correlated with placental vascular abnormalities,
iii) a placental pro-angiogenic factor is able to reach the foetal brain,
iv) the neurodevelopmental abnormalities of brain angiogenesis in FASD children are associated with a dysregulation of the placental PlGF/brain VEGF-R1 system,
v) placental invalidation for PlGF reproduces the effects of foetal alcohol exposure on brain VEGF-R1,
vi) a dysregulation of placental PlGF levels following foetal alcohol exposure makes it possible to predict brain damage,
vii) a placental protein factor, PlGF, was identified as a biomarker of brain damage induced by in utero alcohol exposure.

The invention claimed is:

1. A method of treatment of foetal alcohol spectrum disorders (FASDs) in a subject believed to be suffering from an FASD comprising the following steps:
   a) measuring the amount of placental growth factor (PlGF) in a biological sample from said subject by measuring the amount of the polypeptide;
   b) comparing the amount of PlGF from step a) with a reference;
   c) verifying an FASD in said subject, and
   d) treating a subject verified to have an FASD.

2. The method of claim 1, characterised in that the reference is a measurement of the amount of PlGF in a healthy individual.

3. The method of claim 1, characterised in that an amount of FlGF from step a) lower than the reference indicates that the subject suffers from an FASD.

4. The method of claim 1, characterised in that an amount of PlGF from step a) lower than the reference indicates a brain vascular disorganisation in the subject.

5. The method of claim 1, characterised in that said biological sample is obtained from the placenta.

6. The method of claim 1, characterised in that the amount of PlGF is measured by a method selected from immunohistology, immunoprecipitation, Western blot, dot blot, ELISA or ELISPOT, ECLIA, protein arrays, antibody arrays, or tissue arrays coupled with immunohistochemistry, FRET or BRET techniques, microscopy or histochemistry methods, confocal microscopy and electron microscopy methods, methods based on the use of one or more excitation wavelengths and a suitable optical method, an electrochemical method (voltammetry and amperometry techniques), atomic force microscopy, and radio frequency methods, multipolar resonance spectroscopy, confocal and non-confocal, detection of fluorescence, luminescence, chemiluminescence, absorbance, reflectance, transmittance, and birefringence or refractive index, surface plasmon resonance, ellipsometry, a resonant mirror method, flow cytometry, radioisotope or magnetic resonance imaging, analysis by polyacrylamide gel electrophoresis (SDS-PAGE), HPLC-mass spectrophotometry and liquid chromatography-mass spectrophotometry/mass spectrometry (LC-MS/MS).

7. The method of claim 1, characterised in that the amount of PlGF is determined by a method selected from immunoprecipitation, immunohistology, Western blot, dot blot, ELISA or ELISPOT, ECLIA, protein arrays, antibody arrays, or tissue arrays coupled with immunohistochemistry.

8. The method of claim 1, characterised in that the amount of PlGF is determined by Western blot or by ELISA.

9. The method of claim 1, characterised in that the amount of PlGF is normalised relative to a control marker.

10. The method of claim 9, characterised in that the control marker is a gene selected from the group consisting of β-2 microglobulin gene (B2M), transferrin receptor gene (TFRC), Tyrosine 3-monooxygenase/tryptophan 5-monooxygenase activation protein, zeta polypeptide (YW-HAZ), ribosomal protein LO gene(RPLO), 18S ribosomal RNA, Beta-glucuronidase gene (GUSB), ubiquitin C gene (UBC), Tata Binding Protein gene (TBP), Glyceraldehyde -3-phosphate dehydrogenase gene (GAPDH), peptidylprolyl isomerase A gene (PPIA), DNA-directed RNA polymerase II subunit RPB1 gene (POLR2A), β-actin gene (ACTB), Phosphoglycerate kinase 1 gene (PGK1), hypoxanthine-guanine phosphoribosyltransferase gene (HPRT1), Importin 8 gene (IPO8) and hydroxymethylbilane synthase gene (HMBS), or a polypeptide selected from the products of said genes.

11. The method of claim 1, characterized in that said biological sample is obtained from the cord blood.

\* \* \* \* \*